United States Patent
Pau et al.

(10) Patent No.: US 8,718,741 B2
(45) Date of Patent: *May 6, 2014

(54) EVOKED STAPEDIUS REFLEX THRESHOLD TILE ELECTRODE

(71) Applicant: MED-EL Elektromedizinsche Geraete GmbH, Innsbruck (AT)

(72) Inventors: Hans Wilhelm Pau, Rostock (DE); Detlef Behrend, Rostock-Warnemünde (DE); Mareike Warkentin, Rostock (DE); Wolfram Schmidt, Rostock (DE); Olaf Specht, Rostock (DE); Daniel Schaudel, Innsbruck (AT); Guido Reetz, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/921,270

(22) Filed: Jun. 19, 2013

(65) Prior Publication Data

US 2013/0281812 A1    Oct. 24, 2013

Related U.S. Application Data

(63) Continuation of application No. 13/326,581, filed on Dec. 15, 2011.

(60) Provisional application No. 61/423,717, filed on Dec. 16, 2010.

(51) Int. Cl.
A61B 5/0484    (2006.01)
A61B 5/0476    (2006.01)
A61B 5/04      (2006.01)
A61N 1/00      (2006.01)

(52) U.S. Cl.
USPC ............ 600/379; 600/373; 600/377; 607/137

(58) Field of Classification Search
USPC ................. 600/372–373, 377–379, 386, 393, 600/546–547; 607/137
See application file for complete search history.

(56) References Cited

U.S. PATENT DOCUMENTS

| | | | | | |
|---|---|---|---|---|---|
| 2,423,627 | A | * | 7/1947 | Tinnerman | 439/100 |
| 4,483,338 | A | * | 11/1984 | Bloom et al. | 606/50 |
| 6,208,882 | B1 | | 3/2001 | Lenarz et al. | 300/379 |
| 2010/0268054 | A1 | | 10/2010 | Behrend et al. | 600/373 |
| 2011/0282177 | A1 | * | 11/2011 | Behrend et al. | 600/386 |

FOREIGN PATENT DOCUMENTS

DE    102007026645 A1 * 12/2008 ................. 600/386

* cited by examiner

Primary Examiner — Linda Dvorak
Assistant Examiner — Brian M Antiskay
(74) Attorney, Agent, or Firm — Sunstein Kann Murphy & Timbers LLP

(57) ABSTRACT

An electrode arrangement is described for sensing electrical activity in target tissue. An inner electrode has an elongate electrode body formed as a cylindrical section with an inner penetrating end for insertion into the stapedius muscle target tissue. An outer electrode fits over the inner electrode and an outer penetrating end for insertion into the target tissue. The two electrodes are joined together with their electrode bodies in parallel so that the penetrating ends of the electrodes penetrate in the same direction into the target tissue to sense electrical activity in the target tissue.

5 Claims, 4 Drawing Sheets

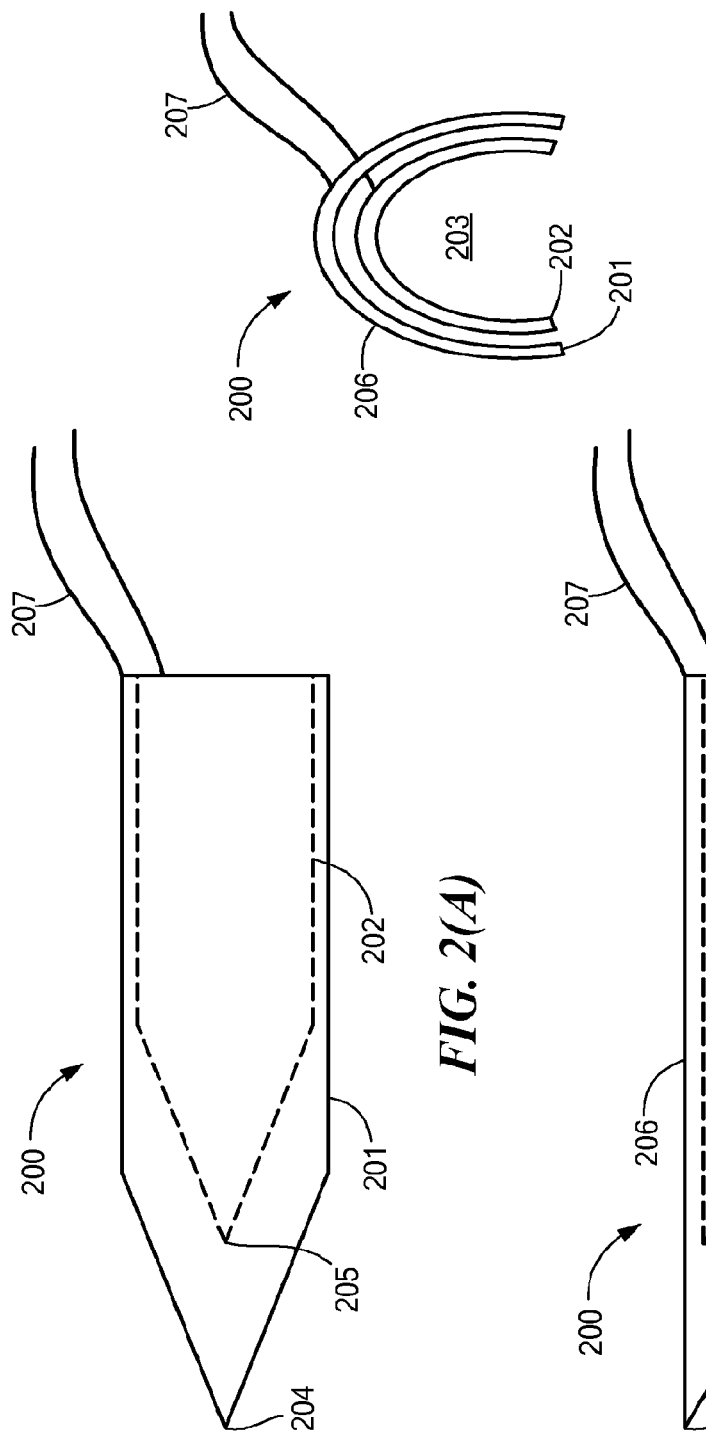

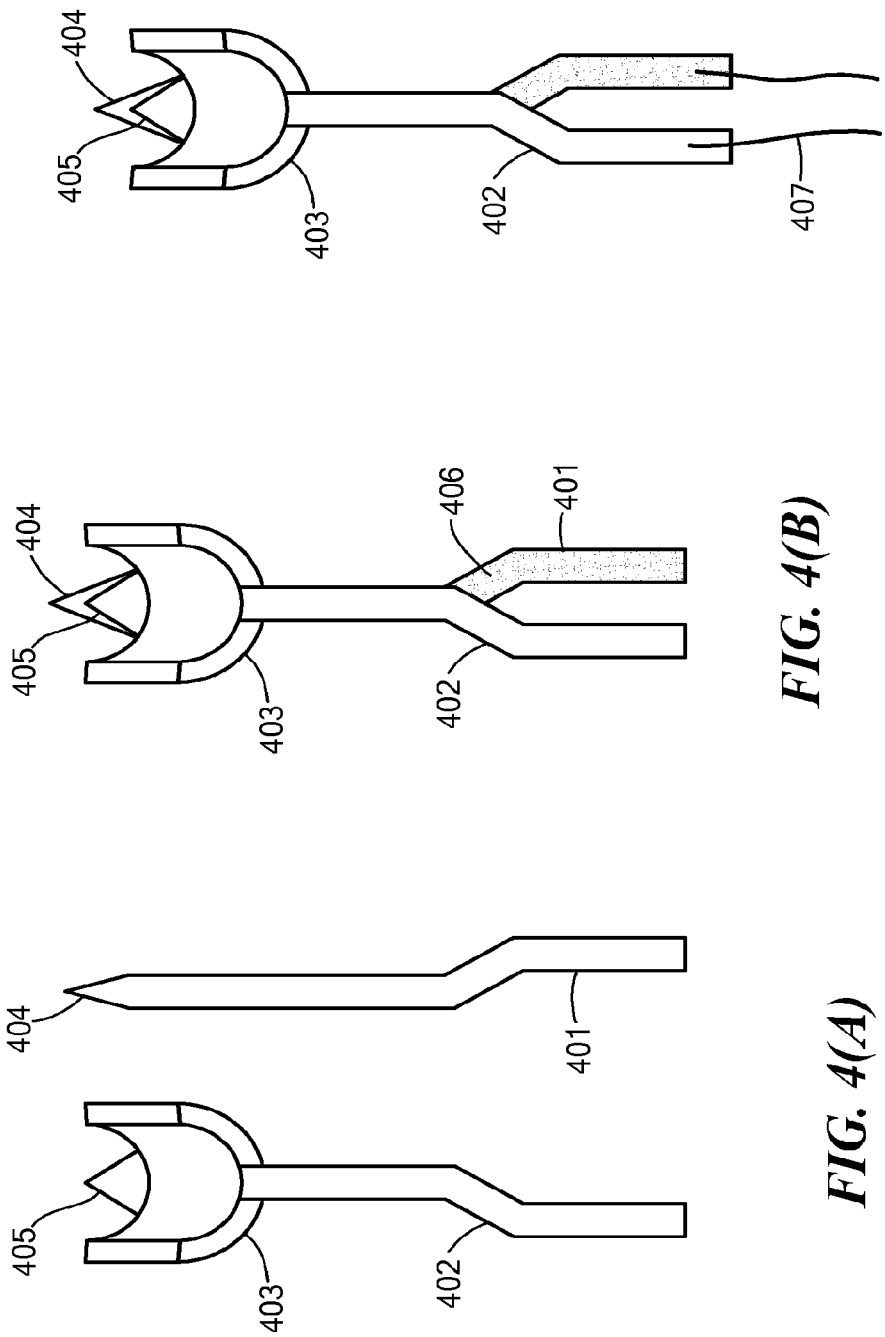

EVOKED STAPEDIUS REFLEX THRESHOLD TILE ELECTRODE

This application is a continuation of U.S. patent application Ser. No. 13/326,581, filed Dec. 15, 2011, which in turn claims priority from U.S. Provisional Patent Application 61/423,717, filed Dec. 16, 2010; both of which are incorporated herein by reference.

TECHNICAL FIELD

The present invention relates to an electrode configuration for measuring the action current and/or the action potential of electrically active tissue, specifically a bipolar stapedius muscle electrode configuration for measuring the action potential generated upon a contraction of the stapedius muscle.

BACKGROUND ART

The human ear may be divided into the outer ear, middle ear, and inner ear. The middle ear includes the eardrum and the auditory ossicles—hammer, anvil, and stirrup. Sound waves entering the outer ear cause the eardrum to oscillate. A mechanical impedance conversion occurs in the middle ear, which allows an optimum transmission of the sound signal from the outer ear to the inner ear. Thus, the ear drum oscillations are transmitted by the ossicles to the oval window of the inner ear which vibrates the fluid within the cochlea. Hair cells projecting into the cochlea are bent by the vibration of the cochlear fluid, thereby triggering nerve pulses.

The middle ear also contains the tympanic muscle and the stapedius muscle. The tympanic muscle is linked to the hammer, the stapedius muscle being connected via a tendon to the stirrup. In case of an excessively high sound pressure which could damage the inner ear, both muscles contract reflexively to decrease the mechanical coupling of the eardrum to the inner ear (and thereby also the force transmission). This protects the inner ear from excessively high sound pressures. This tensing of the stapedius muscle when triggered by high sound pressures is also referred to as the stapedius reflex. Medically relevant information about the functional capability of the ear may be obtained from the diagnosis of the stapedius reflex. The measurement of the stapedius reflex also is useful for setting and/or calibrating cochlear implants, because the sound energy perceived by a patient may be deduced from the measured stapedius reflex.

The stapedius reflex can be determined in a post-operative clinical setting using an acoustic tympanometer which also requires another additional device to take and use the electrical measurements. To measure the stapedius reflex, it is known to intra-operatively use electrodes that are brought into contact with the stapedius muscle to relay to a measuring device the action current and/or action potentials generated upon a contraction of the stapedius muscle. A reliable minimally-invasive contact of the stapedius muscle is difficult because the stapedius muscle is situated inside a trough present in a bone and only the tendon of the stapedius muscle connected to the stirrup and its upper part are accessible from the interior of the middle ear.

Various intraoperative stapedius muscle electrodes are known from U.S. Pat. No. 6,208,882, however, these only achieve inadequate contact of the stapedius muscle tissue (in particular upon muscle contraction) and are also very traumatizing. In order to make ESRT measurements simpler and quicker, first non-commercial intraoperative experiments and studies have been conducted with monopolar (Almqvist et al. 2000) or bipolar hook electrodes (Pau et al. 2008), respectively, which have been attached at the stapedius tendon or muscle to measure the muscle activity in the case of a reflex. The measurements were successful, but the electrode design was only suitable for intra-operative tests. The Almqvist hook electrode does not allow a quick and easy placement at the stapedius tendon and muscle—the electrode has to be hand held during intra-operative measurements. the Pau bipolar hook electrode does not ensure that that both electrodes are inserted into the stapedius muscle due to the small dimensions of the muscle and the flexibility of the electrode tips. One weakness of these electrodes is that they do not qualify for chronic implantation.

DE 10 2007 026 645 A1 discloses a two-part bipolar electrode configuration where a first electrode is pushed onto the tendon of the stapedius muscle or onto the stapedius muscle itself, and a second electrode is pierced through the first electrode into the stapedius muscle. One disadvantage of the described solution is its rather complicated handling in the very limited space of a surgical operation area, especially manipulation of the fixation electrode. In addition, the piercing depth of the second electrode is not controlled so that trauma can also occur with this approach.

U.S. patent application Ser. No. 12/763,374, filed Apr. 20, 2010 (incorporated herein by reference) describes an electrode arrangement 100 as shown in FIG. 1 for sensing electrical activity in target tissue. A support electrode 101 has an elongate electrode body with a base end 102 and a penetrating end 103 for insertion into the target tissue. A fixation electrode 104 has an elongate electrode body with a base end 105 and a penetrating end 106 at an angle to the electrode body. The penetrating electrode 104 passes perpendicularly through an electrode opening 107 in the support electrode 101 so that the penetrating ends 103 and 106 of the electrodes penetrate into the target tissue so that at least one of the electrodes senses electrical activity in the target tissue.

It would be advantageous to have a simple cost effective electrode for measuring action currents and/or action potentials in electrically active tissues (such as the stapedius muscle tissue), which enables secure but reversible fixing of the electrode in the target tissue, but which traumatizes the tissue as little as possible.

SUMMARY

Embodiments of the present invention are directed to an electrically elicited stapedius reflex threshold (ESRT) tile electrode arrangement for sensing electrical activity in target tissue such as the stapedius muscle. An inner electrode has an elongate electrode body formed as a hollow cylinder section with an inner penetrating end for insertion into the target tissue. An outer electrode fits over the inner electrode and has an outer penetrating end for insertion into the target tissue. The two electrodes are joined together with their electrode bodies in parallel so that the penetrating ends of the electrodes penetrate in the same direction into the target tissue to sense electrical activity in the target tissue.

The electrodes may be arranged to have the outer penetrating end penetrate into the target tissue before the inner penetrating end, or to have the inner penetrating end penetrate into the target tissue before the outer penetrating end. There may also be an insulation layer arranged between the electrodes to electrically isolate the electrodes from each other. The arrangement may include an electrically elicited stapedius reflex threshold (ESRT) sensing arrangement.

Embodiments of the present invention also include an electrode fixation structure for securing an implantable electrode sensing arrangement. An implantable fixation bar of deformable material has attachment openings at opposing ends for securing the opposing ends to underlying bone. A lead holder is connected to the fixation bar for holding wire leads of the electrode sensing arrangement in a defined position.

The lead holder may be based on a ring shape. The fixation bar may be made of a deformable metal material. The implantable electrode sensing arrangement may include an electrically elicited stapedius reflex threshold (ESRT) sensing arrangement.

BRIEF DESCRIPTION OF THE DRAWINGS

FIG. 2 A-C shows an Evoked Stapedius Reflex Threshold (ESRT) Tile Electrode according to one embodiment of the present invention.

FIG. 4 A-C shows assembly of an ESRT Tile electrode according to one embodiment of the present invention.

DETAILED DESCRIPTION

Figure 1:
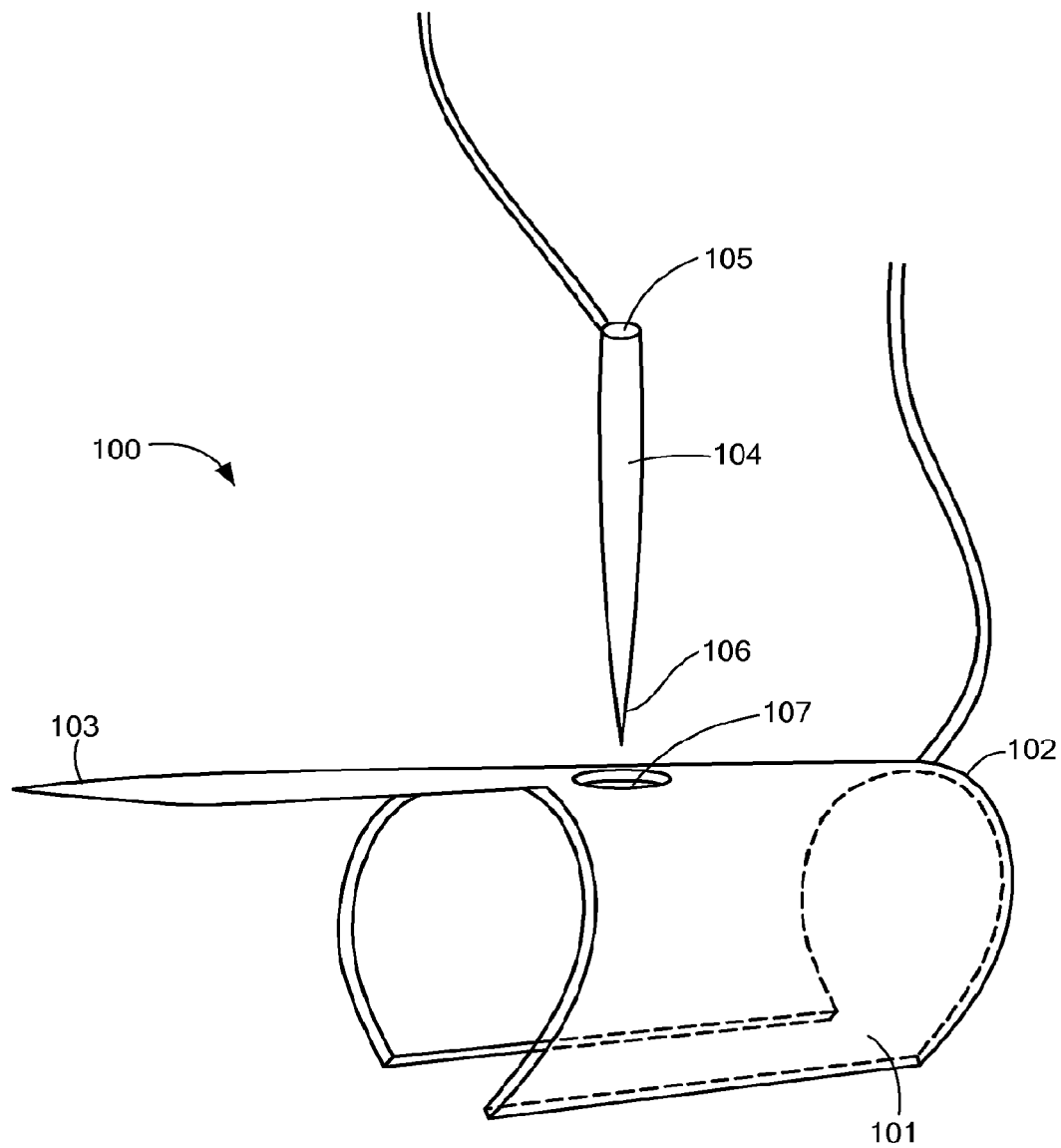
FIG. 1 shows an electrode arrangement for sensing electrical activity in target tissue as is known in the prior art.

Various embodiments of the present invention are directed to an Evoked Stapedius Reflex Threshold (ESRT) Tile Electrode arrangement for sensing electrical activity in the stapedius muscle. Two matching half shell cylindrical section electrode structures have parallel electrode bodies with penetrating ends of the electrodes that penetrate into the stapedius muscle in the same direction. An electrode fixation structure can secure the electrode arrangement in place.

For example, FIG. 2 A-C shows one specific embodiment of an ESRT Tile Electrode 200. An inner electrode 202 has an elongate electrode body formed as a hollow cylinder section with an inner penetrating end 205 for insertion into the target tissue. An outer electrode 201 fits over the inner electrode 202 and also has an outer penetrating end 204 for insertion into the stapedius muscle target tissue. In order to optimize the active electrical surface of penetrating ends 204 and 205, a rough surface such as a fractal coating may be useful to provide for a proper recording over a prolonged implantation time which may include tissue growth over the electrode surfaces and consequent lowering of the phase interface impedance.

The rear part of each electrode 201 and 202 forms a flat thin tail which provides a stable elongation for surgical handling, allowing, for example, fixation of the Tile Electrode 200 in the posterior tympanotomy by bending the elongated tail portion of the electrodes 201 and 202 into an appropriate position with respect to the bony bridge. The tails of the electrodes 201 and 202 also provides a good location for connecting to the electrode wires 207 back to the implant processor (stimulator).

The two electrodes 201 and 202 are joined together with their electrode bodies in parallel so that the penetrating ends 204 and 205 penetrate in the same direction into the target tissue. In the embodiment shown in FIG. 2, the outer penetrating end 204 penetrates into the target tissue before the inner penetrating end 205. In other embodiments, it may be the other way round with the inner penetrating end 205 penetrating into the target tissue before the outer penetrating end 205. In the specific embodiment shown in FIG. 2, the penetrating ends 204 and 205 are axially displaced from each other by around one third of the total length of the electrodes 201 and 202, allowing them to behave as two separate independent electrodes.

Both electrodes 201 and 202 can be radially displaced from each other as well as longitudinally to come up with a proper EMG recording. For example, in the embodiment shown in FIGS. 2B and 2C, there also is an insulation layer 206 arranged between the electrodes 201 and 202 to electrically isolate them from each other. The resulting radial spatial displacement of the two electrodes 201 and 202 allows for bipolar recordings.

The arrangement of the Tile Electrode 200 allows an easy and quick surgical placement at the stapedius tendon, which then can be moved into the stapedius muscle. The compact and robust design of the Tile Electrode 200 enables the simultaneous insertion of the penetrating ends 204 and 205 of both electrodes 201 and 202 into the stapedius muscle target tissue despite the small size of the muscle itself Compared to the prior art electrode arrangement shown in FIG. 1, the present Tile Electrode 200 does not require any penetration holes in the electrodes 201 and 202, nor does surgical implantation of the Tile Electrode 200 require the complicated insertion of a fixation electrode perpendicular to the main electrode body, thereby saving considerable time during the surgical implantation of the device.

Figure 3A:
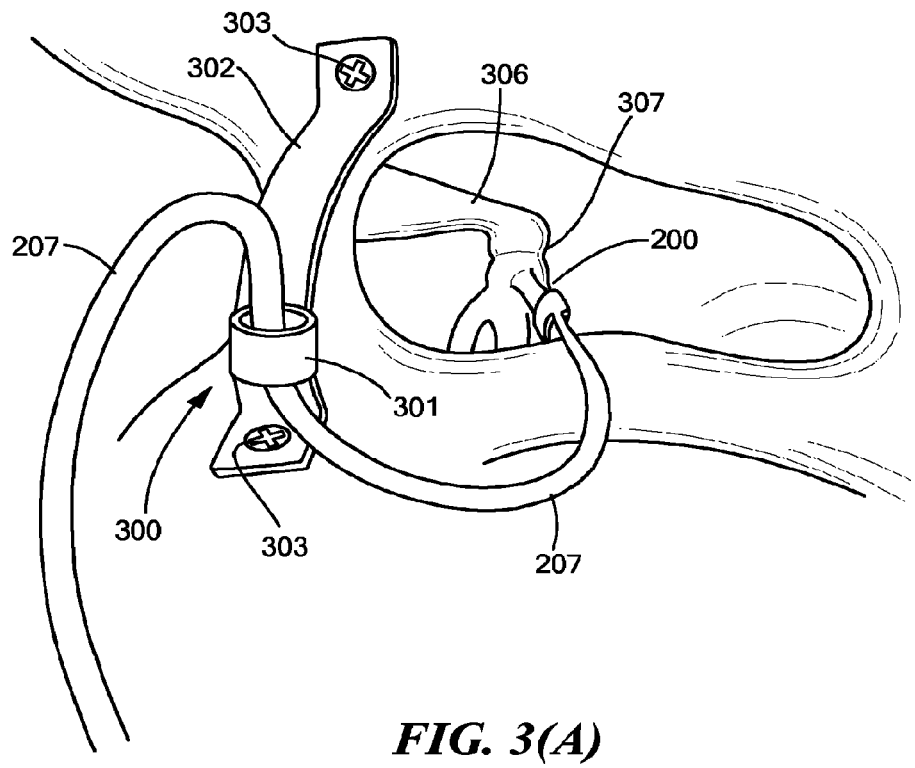
FIG. 3 A-B shows an electrode lead holder according to one embodiment of the present invention.
Figure 3B:
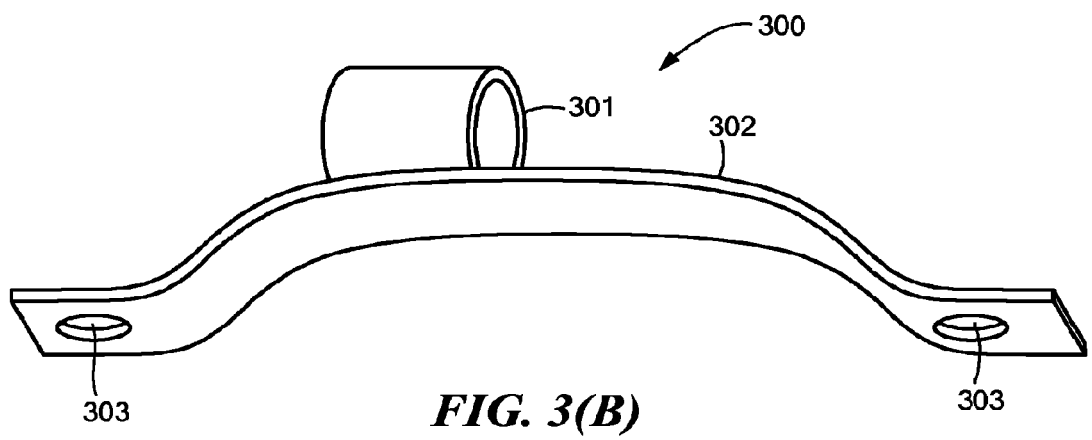

FIG. 3 A-B shows an electrode lead holder 300 according to one embodiment of the present invention which acts as an electrode fixation structure to facilitate securing of the electrode sensing arrangement in a desired fixed position within the middle ear. In the embodiment shown in FIG. 3, an implantable fixation bar 302 is made of some deformable material such as soft metal so it can be bent as desired during surgical implantation. The fixation bar 302 includes attachment openings 303 at opposing ends for securing the fixation bar 302 to underlying bone. A lead holder 301 is connected to the fixation bar 302 for holding wire leads of the electrode sensing arrangement in a defined position. In the embodiment shown in FIG. 3, the lead holder 301 is in the specific form of a cylindrical ring.

During surgery to implant the electrode, the surgeon would place the electrode lead holder 300 first, attaching it firmly to a middle ear bony structure (such as the bone bridge in front of the incus, or on the incus, or on the middle ear wall such as on the promontory). The electrode lead holder 300 avoids placing tension on the connecting electrode wires and on the stapedius tendon and/or muscle, thereby helps to keep the electrode structure in place.

When the electrode lead holder 300 has been brought into proper position, the electrode sensing arrangement then can be adjusted to its final position. Once the arrangement is installed, the electrode lead holder 300 can permanently hold the electrode sensing arrangement in its implanted position to reliably record signals over several months or years. In some embodiments, the electrode lead holder 300 may also serve as a reference electrode or as a second sensing electrode where the muscle/tendon electrode is a single electrode.

The fixation structure of the electrode lead holder 300 helps avoid damage to the electrode sensing arrangement during implantation: The electrode lead holder 300 can be manipulated with a forceps or another surgical instrument and thus allow the surgeon to bring it into position. This can occur without direct contact of the surgeon's instrument to the more delicate electrode structure which is therefore less likely to be damaged by the surgeon's instrument.

FIG. 4 A-C shows assembly of an ESRT Tile electrode according to one embodiment of the present invention. Initially the inner electrode 402 on the left side of FIG. 4A and the outer electrode 401 on the right side are separate structures. Side wings 403 are bent into a curve adapted to fit around the target tissue (muscle or tendon) where the electrode is ultimately to be placed. Then the outer top side of the inner electrode 402 (the back side in this view) and/or the inner bottom side of the outer electrode 401 (the front side in this view) are sprayed with a layer of insulation material 406, e.g., silicone, and the two electrodes 401 and 402 are fit together over the wet insulation, FIG. 4B. The insulation material 406 is cured for a period, e.g., 30 minutes at 120° C., then more insulation material 406 may be applied to the remainder of the electrode and cured. Portions of the inner electrode 402 and outer electrode 401 may be masked while the insulation material 406 is applied. After assembly and insulation, the masking may be removed to expose bare metal from desired parts of the electrodes 401 and 402 such as the penetrating ends 404 and 405 and/or the tail pieces where connecting wires 407 may be soldered or welded on.

Although various exemplary embodiments of the invention have been disclosed, it should be apparent to those skilled in the art that various changes and modifications can be made which will achieve some of the advantages of the invention without departing from the true scope of the invention.

What is claimed is:

1. An electrode arrangement for sensing electrical activity in target tissue, the arrangement comprising:
    an inner electrode having an elongate electrode body formed as a hollow partial cylinder section with an inner penetrating end for insertion into the target tissue and an inner surface configured to lie over the target tissue; and
    an outer electrode fitting over the inner electrode and having an outer penetrating end for insertion into the target tissue;
    wherein the inner and outer electrodes are joined together with their electrode bodies in parallel so that the inner and outer penetrating ends penetrate in the same direction into the target tissue to sense electrical activity in the target tissue.

2. An electrode arrangement according to claim 1, wherein the electrodes are arranged to have the outer penetrating end penetrate into the target tissue before the inner penetrating end.

3. An electrode arrangement according to claim 1, wherein the electrodes are arranged to have the inner penetrating end penetrate into the target tissue before the outer penetrating end.

4. An electrode arrangement according to claim 1, further comprising:
    an insulation layer arranged between the electrodes to electrically isolate the electrodes from each other.

5. An electrode arrangement according to claim 1, wherein the arrangement comprises an electrically elicited stapedius reflex threshold (ESRT) sensing arrangement.

* * * * *